United States Patent [19]
Rand et al.

[11] Patent Number: 5,719,914
[45] Date of Patent: Feb. 17, 1998

[54] METHOD FOR CORRECTING SPHERICAL ABERRATION OF THE ELECTRON BEAM IN A SCANNING ELECTRON BEAM COMPUTED TOMOGRAPHY SYSTEM

[75] Inventors: Roy E. Rand, Palo Alto; Khem Garewal, San Ramon; Glenn R. James, Pleasant Hill, all of Calif.

[73] Assignee: Imatron, Inc., So. San Francisco, Calif.

[21] Appl. No.: 557,969

[22] Filed: Nov. 13, 1995

[51] Int. Cl.$^6$ .................................................. G01N 23/00
[52] U.S. Cl. .................................................. 378/4; 378/10
[58] Field of Search .................................................. 378/4, 10

[56] References Cited

U.S. PATENT DOCUMENTS 5,386,445  1/1995  Rand et al.

*Primary Examiner*—Craig E. Church
*Attorney, Agent, or Firm*—Flehr Hohbach Test Albritton & Herbert LLP

[57] ABSTRACT

In a scanning electron beam CT system, spherical aberration of the electron self-forces produces a deleterious halo around the final electron beam spot, causing loss of definition in the image rendered by the system. The spherical aberration is caused by non-uniform electron beam current density, and by non-uniform distribution of positive ions in the transition region of the beam-optical systems. The non-uniform electron beam current density depends upon the axial position of the electron gun cathode, while the transition region ion distribution depends upon the potential coupled to the washer-shaped positive ion electrode ("PIE") used to segregate the upstream and downstream portions of the electron beam. In the present invention, the beam spot halo is minimized (if not eliminated), and image definition is maximized by selecting the electron gun cathode axial position and the PIE potential such that their contributions to spherical aberrations at the final beam spot cancel.

9 Claims, 11 Drawing Sheets

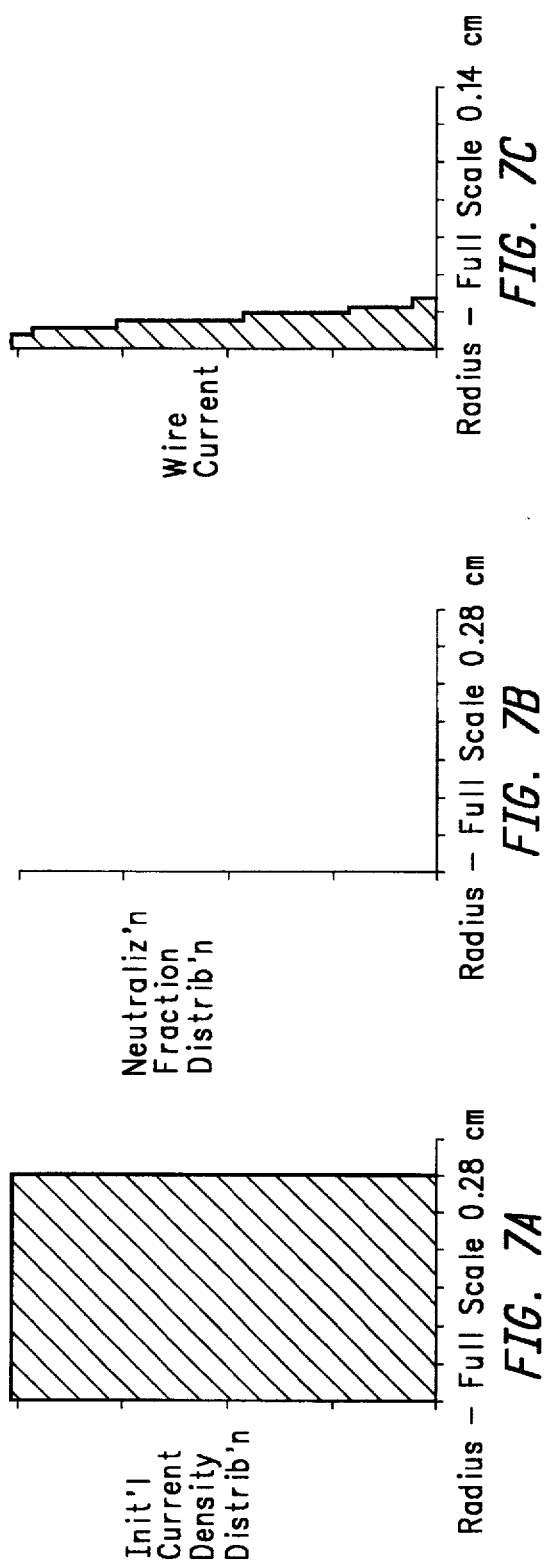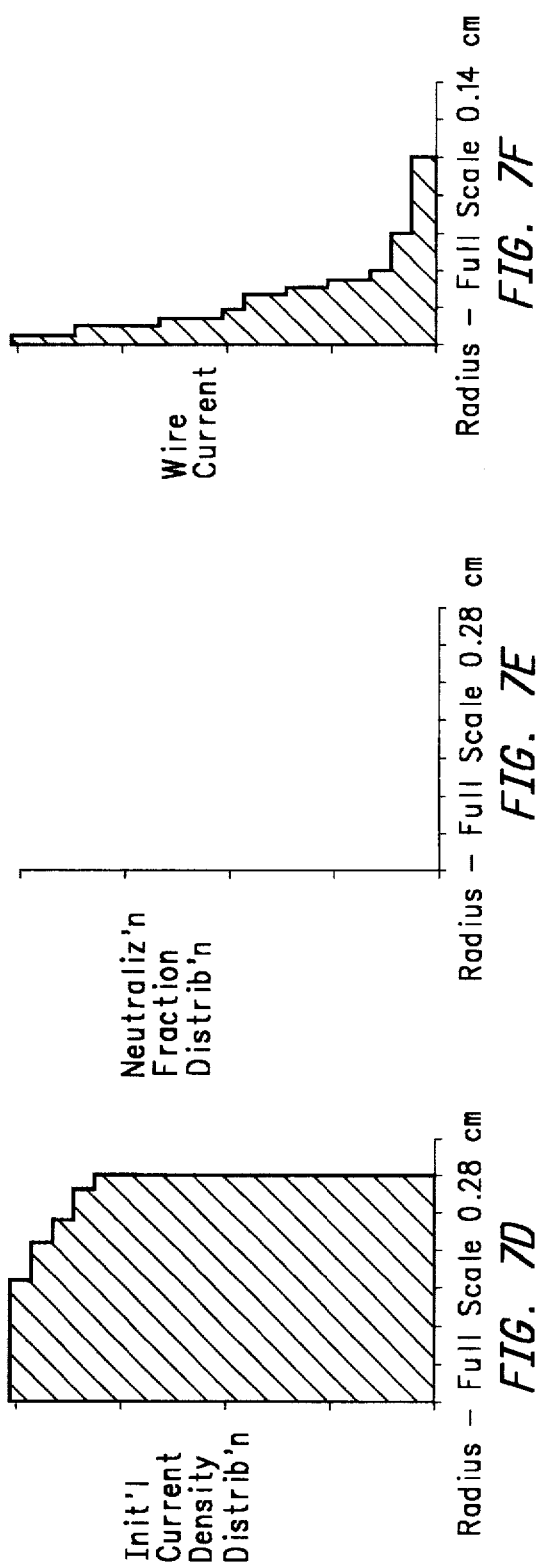

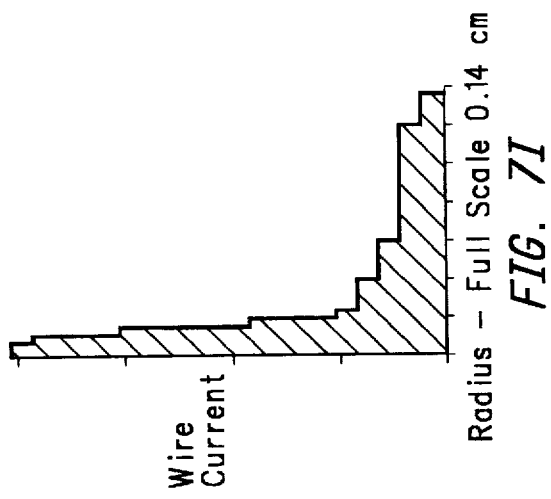
FIG. 7G
FIG. 7H
FIG. 7I
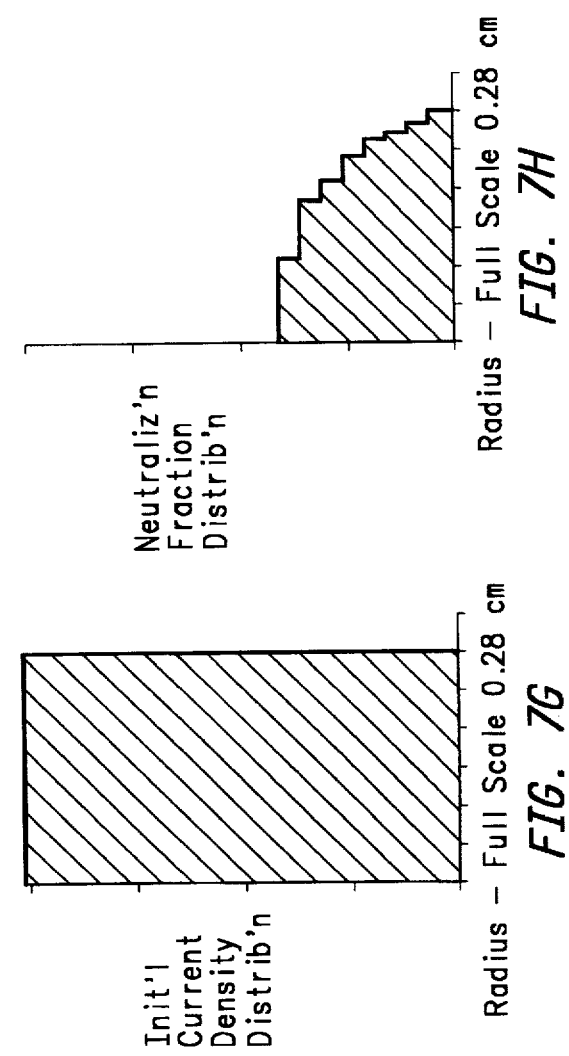
FIG. 7J
FIG. 7K
FIG. 7L

METHOD FOR CORRECTING SPHERICAL ABERRATION OF THE ELECTRON BEAM IN A SCANNING ELECTRON BEAM COMPUTED TOMOGRAPHY SYSTEM

FIELD OF THE INVENTION

The present invention relates generally to improving image definition in scanning electron beam computed tomographic X-ray systems, and more particularly to correcting spherical aberration of the electron beam in such systems.

BACKGROUND OF THE INVENTION

Scanning electron beam computed tomography ("CT") systems are described generally in U.S. Pat. No. 4,352,021 to Boyd, et al. (Sep. 28, 1982), and U.S. Pat. No. 4,521,900 (Jun. 4, 1985), U.S. Pat. No. 4,521,901 (Jun. 4, 1985), U.S. Pat. No. 4,625,150 (Nov. 25, 1986), U.S. Pat. No. 4,644,168 (Feb. 17, 1987), U.S. Pat. No. 5,193,105 (Mar. 9, 1993), and U.S. Pat. No. 5,289,519 (Feb. 22, 1994), all to Rand, et. al. Applicants refer to and incorporate herein by reference each above listed patent to Rand, et al.

As described in the above-referenced Rand et al. patents, an electron beam is produced by an electron gun at the upstream end of an evacuated generally conical shaped housing chamber. A large negative potential (e.g., −130 kV) on the electron gun cathode accelerates the electron beam downstream along the chamber axis. Further downstream, a beam optical system that includes magnetic focusing, quadrupole, and deflection coils focuses and deflects the beam to scan along an X-ray producing target. The final beam spot at the X-ray producing target is smaller than that produced at the electron gun, and must be suitably sharp and halo-free, so as not to degrade definition in the image rendered by the system.

The X-rays produced by the target penetrate a patient or other object and are detected by an array of detectors. The detector array, like the target, is coaxial with and defines a plane orthogonal to the system axis of symmetry. The output from the detector array is digitized, stored, and computer processed to produce a reconstructed X-ray video image of a portion of the object, typically an image of a patient's anatomy.

In the chamber region upstream of the beam optical system, a diverging beam is desired and the electron beam can advantageously self-expand due to the force created by its own space-charge. By contrast, downstream from the beam optical system, a converging, self-focusing, beam is desired to minimize the final beam spot at the X-ray producing target.

As the electron beam passes through the vacuum chamber, it ionizes residual or introduced gas therein, producing positive ions. The positive ions are useful in the down-stream chamber region where space-charge neutralization and a converging beam are desired. But in the upstream region, unless removed by an external electrostatic field, the positive ions are trapped in the negative electron beam. The space-charge needed for the desired beam self-expansion may undesirably be neutralized, and the beam may even destabilize or collapse.

As described in U.S. Pat. Nos. 4,625,150, 5,193,105, and 5,289,519, the positive ions may be removed from the beam using a device that creates transverse electric fields in the region between the electron gun and the beam-optical lens system (magnetic solenoid). One form of this device is a rotatable ion clearing electrode assembly, and is referred to as a "RICE" unit.

Alternatively, as disclosed in U.S. Pat. No. 5,386,445, the positive ions may be removed from the beam using washer-shaped disk-like elements that create alternating axial electric fields in the region between the electron gun and the beam-optical lens system (magnetic solenoid). The assembly of disk-like elements if referred to as a periodic ion clearing electrode ("PICE") unit.

Using such transverse and/or alternating axial electric fields to remove positive ions between the electron gun and the beam optical lens system advantageously produces an electron beam that is self-repulsive (or self-defocusing) in the upstream or first region, and that is self-attractive (or self-focusing) in the downstream or second region.

The first and second regions are segregated preferably by a washer-shaped positive ion electrode (or "PIE"), typically coupled to a high positive potential, e.g., +2.5 kV, as disclosed in U.S. Pat. Nos. 5,193,105, 5,289,419 and 5,386,445. The magnitude of the PIE potential can be used to determine the relative lengths of the upstream and downstream beam regions. Further, a suitably high PIE potential prevents ions created downstream from drifting into the upstream region.

One problem that has been encountered with systems as described above is spherical aberration, which is due to non-linearity of the electron beam self-forces. These aberrations cause the final electron beam spot at the X-ray producing target to be surrounded by a halo. Because the beam spot at the X-ray producing target is the source of X-rays, the source X-rays will also possess a halo. The unfortunate result is a loss of definition in anatomical and other images rendered with the scanning electron beam system.

Thus, there is a need for a method to reduce such spherical aberrations in an electron beam computed tomographic scanner system.

The present invention discloses such a method.

SUMMARY OF THE INVENTION

Scanning electron beam computed tomography systems have upstream and downstream regions of differing beam neutralization, the regions being separated by a positive ion electrode ("PIE"). The present invention recognizes that spherical aberration in such systems results from non-uniform electron beam current density, and from the distribution of positive ions in the transition region of the beam-optical system. Non-uniform electron beam current density depends upon the axial position of the electron gun cathode, whereas transition region ion distribution depends upon the PIE electrostatic potential.

Beam spot haloes due to spherical aberration are minimized in the present invention by positioning the electron gun cathode and by selecting the PIE potential such that their contributions to spherical aberrations cancel. Typically the PIE potential required to reduce haloes is in the range of a few hundred volts, the optimum PIE potential being determined while viewing the beam spot profile with a monitoring wire, or the like. In this fashion, the halo and its detrimental effect upon definition of the image rendered by the scanning system is reduced, and manufacturing and positioning tolerances of the electron gun may be relaxed. Because changes in the PIE potential can de-focus the electron beam, a magnetic solenoid lens or other independent focusing element may be used to help focus the final beam spot.

Other features and advantages of the invention will appear from the following description in which the preferred embodiments have been set forth in detail in conjunction with the accompanying drawings.

BRIEF DESCRIPTION OF THE DRAWINGS

FIGS. 7A–7C depict computer simulations, respectively, of initial beam current density distribution, transition region radial neutralization distribution, and an Abel transform of the final beam spot target-location current density distribution, for an ideal initial uniform beam with zero transition region neutralization, according to the present invention;

FIGS. 7D, 7E, 7F depict computer simulations, respectively, of initial beam current density distribution, transition region radial neutralization distribution, and an Abel transform of the final beam spot target-location current density distribution, for an initial beam with a domed parabolic radial beam current density distribution with zero transition region neutralization, according to the present invention;

FIGS. 7G, 7H, 7I depict computer simulations, respectively, of initial beam current density distribution, transition region radial neutralization distribution, and an Abel transform of the final beam spot target-location current density distribution, for an ideal initial uniform beam with a parabolic transition region distribution of neutralization, according to the present invention;

FIGS. 7J, 7K, 7L depict computer simulations, respectively, of initial beam current density distribution, transition region radial neutralization distribution, and an Abel transform of the final beam spot target-location current density distribution, for a domed parabolic radial beam current density distribution selected with the parabolic transition region neutralization distribution to minimize final beam spot halo, according to the present invention;

DESCRIPTION OF THE PREFERRED EMBODIMENTS

Figure 1:
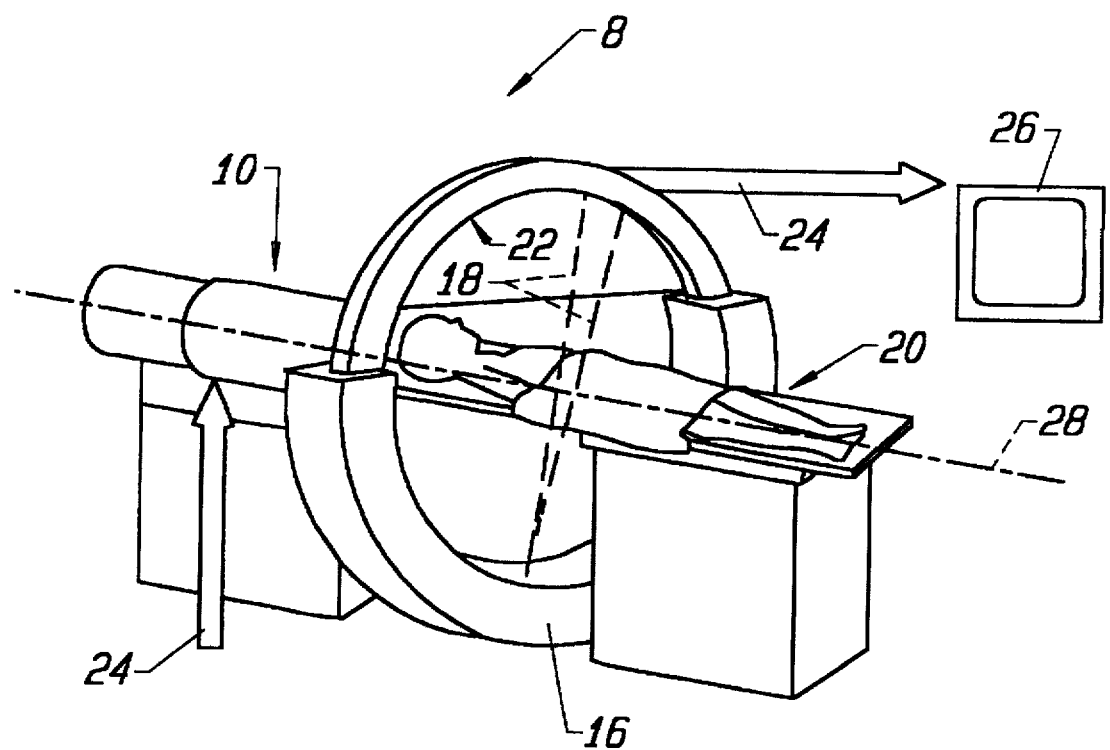
FIG. 1 depicts a generalized scanning electron beam computed tomography X-ray system, with which the present invention may be practiced.
Figure 2:
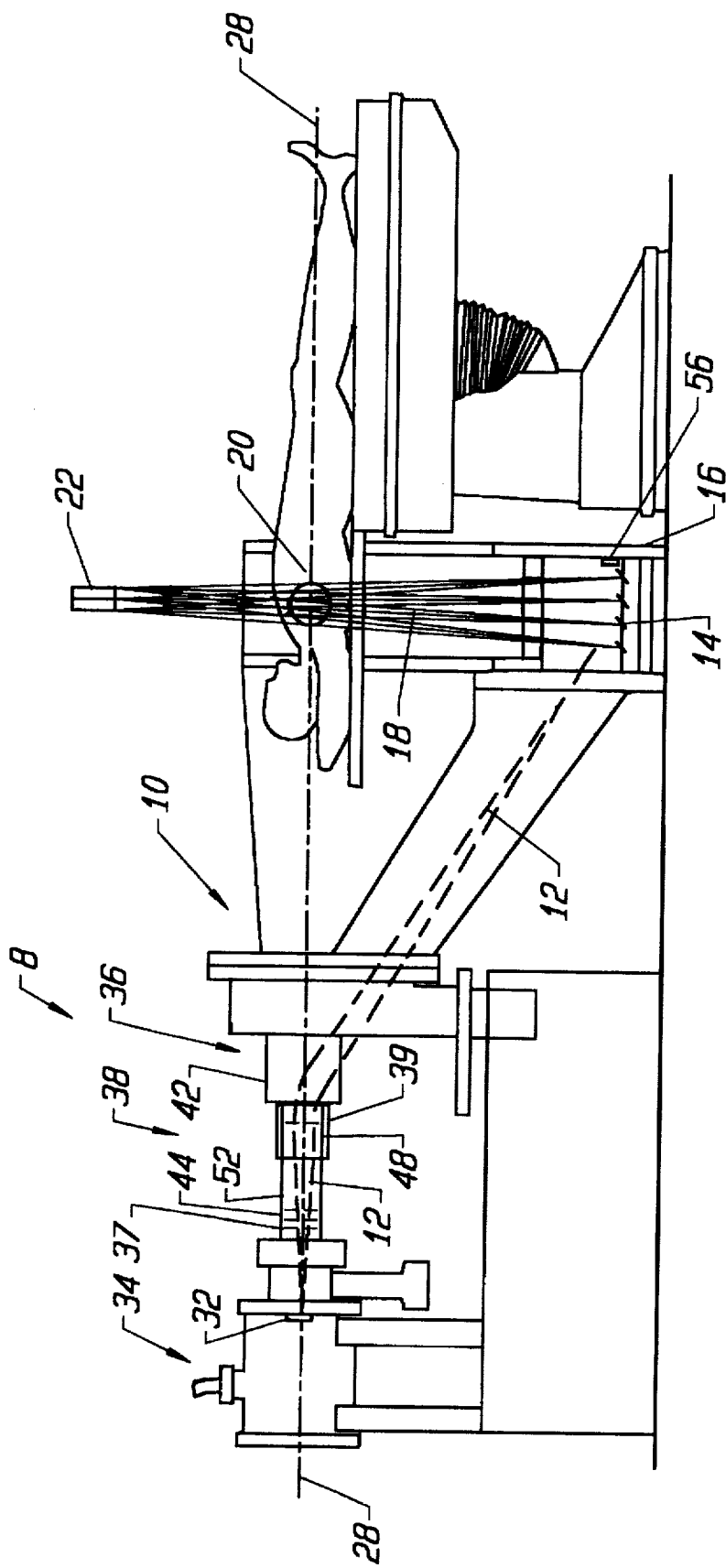
FIG. 2 is a longitudinal cut-away view of the system shown in FIG. 1.

Before describing the present invention per se, it is helpful to understand the operation of a scanning electron beam computed tomographic X-ray system. FIG. 1 and FIG. 2 depict a generalized such system 8, in which spherical aberration is to be corrected if not eliminated, according to the present invention. System 8 includes a vacuum chamber housing 10 in which an electron beam 12 is generated at the cathode of an electron gun 32 located in upstream region 34, in response to perhaps −130 kV high voltage. The electron beam is then caused by optical system 38, including magnetic lens 39 and deflection coil 42, to scan at least one circular target 14 located within a front lower portion 16 of housing 10.

When scanned by the focused electron beam 12, the target 14 emits a moving fan-like beam of X-rays 18. X-rays 18 then pass through a region of a subject 20 (e.g., a patient or other object) and register upon a detector array 22 located diametrically opposite. The detector array outputs data to a computer system (indicated by arrows 24 in FIG. 1) that processes and records the data, producing an image of a slice of the subject on a video monitor 26. As indicated by the second arrow 24, the computer system also controls the system 8 and the electron beam production therein.

Gases in housing 10 produce positive ions in the presence of the electron beam 12. Positive ions are beneficial in the downstream, self-focusing region 36, but must be removed (or at least be suitably controlled) in the upstream, self-expanding de-focusing region 34.

Beam optical system 38 is mounted outside and within housing 10 and includes magnetic lens 39, deflecting coils and quadrupole coils (collectively coils 42), and an electrode assembly 44. Coils 39 and 42 contribute a focusing effect to help shape the final beam spot as it scans one of the targets 14. Electrode assembly 44 controls positive ions in the upstream region.

As will be described, the final electron spot that scans target 14 may, but for the present invention, be surrounded by a halo that results from spherical aberrations or non-linearities of the electron beam self-forces. Unless suitably minimized, the halo will degrade the definition of the image of the object 20 that is rendered by system 8.

Electrode assembly 44 is mounted within housing 10 between the electron gun 32 and the beam optical assembly 38 such that the electron beam 12 passes axially through assembly 44 along the Z-axis 28. Ideally the Z-axis 28 is coaxial with the electron beam 12 upstream from the beam optics assembly 38 within chamber 10. Axis 28 also represents the longitudinal axis of chamber 10, and the axis of symmetry for the electrode assembly 44 and the beam optics assembly 38.

Figure 3:
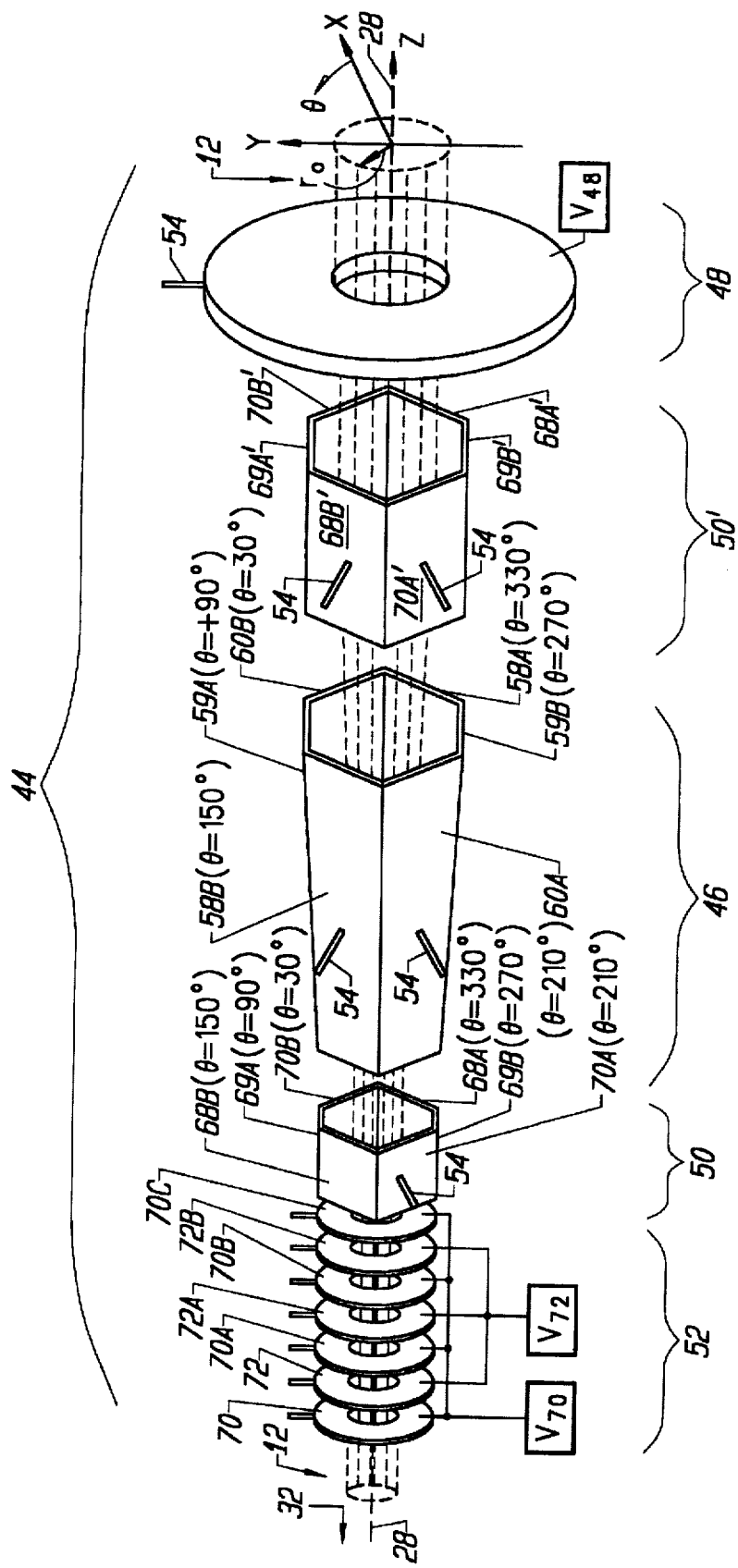
FIG. 3 is a perspective view depicting typical electrodes that may be present in an electrode assembly in the beam optical assembly of the system of FIG. 1.

Referring to FIG. 3, electrode assembly 44 may include a rotatable field ion clearing electrode 46 ("RICE"), a positive ion electrode 48 ("PIE"), first and second ion clearing electrodes 50, 50' ("ICEs"), and a periodic axial field ion controlling electrode 52 ("PICE"). The various PICE, ICE, RICE and PIE electrodes are mounted within housing 10 between the electron gun 32 and coils 39 and 42 such that the electron beam 12 passes axially therethrough about axis 28. The various RICE, PIE, ICE and PICE elements comprising assembly 44 preferably are stainless steel, copper, or other material that does not outgas into chamber 10. These elements are mounted within chamber 10 using insulated standoffs 54, and are coupled to potential sources to produce electric fields.

Although FIG. 3 depicts assembly 44 as including a RICE 46, a PIE 48, two ICEs 50, 50', and a PICE 52 electrode, spherical aberration correction according to the present invention may be accomplished without using all of these electrodes. For example, the PICE 52 may be dispensed with, or the ICE 50, 50' and/or RICE 46 electrodes may be dispensed with, as disclosed in U.S. Pat. No. 5,386,445 to Rand. Whatever elements are dispensed with, ion clearing electric fields must be present between the electron gun and the PIE.

Again referring to FIG. 3, PIE 48 is preferably a planar washer whose center opening is at least as large as the electron beam diameter at that region, typically about 3 cm. As disclosed in U.S. Pat. No. 5,386,445 to Rand, PIE 48 preferably is coupled to a large positive potential (e.g., +2.5 kV) $V_{48}$. The PIE produces an axial field that prevents positive ions from migrating up-stream, which migration would interfere with the production of a sharply self-focused beam spot at the X-ray target. PIE 48 also sharply defines the interface between the upstream region and the downstream region.

PIE 48 segregates the upstream region (e.g., the beam expanding or de-focusing region) from the downstream region (e.g., the beam converging or self-focusing region). Because positive ions exist downstream from PIE 48 (e.g., to the right in FIG. 3), the electron space-charge is neutralized and the beam will converge or self-focus toward axis 28 due to the beam's self-magnetic field. The magnitude of the self-focusing force will vary along axis 28 as a function of the beam diameter and current density, which produces the self-magnetic field.

RICE element 46 and ICE elements 50, 50', disclosed in U.S. Pat. No. 4,625,150 to Rand, et al., function to sweep away positive ions while maintaining a uniform electric field.

Alternatively, positive ions may be removed from the upstream region 34 using a PICE 52, disposed adjacent electron gun 32 and upstream from PIE 48, as shown in FIG. 3. PICE 52 preferably comprises a plurality of disk-like elements 70, 72 spaced apart coaxially along axis 28. Alternate PICE electrodes, e.g., 70, 70A, 70B, 70C are together coupled to a first potential source $V_{70}$, and the intermediate electrodes, e.g., 72, 72A, 72B are together coupled to a second potential source $V_{72}$. In the embodiment of FIG. 3, seven PICE disks are used, $V_{70} \approx -2$ kV and $V_{72} \approx 0$ V (e.g., ground), although other potentials could be used, including possibly +2 kV and ground.

Upstream (e.g., to the left) from PIE 48, positive ions are removed by electrode assembly 44. This permits the electron beam 12 to expand or de-focus due to space-charge of the electrons within the beam. The magnitude of the de-focusing force at various points along axis 28 will vary with the beam diameter and space-charge density.

Figure 4:
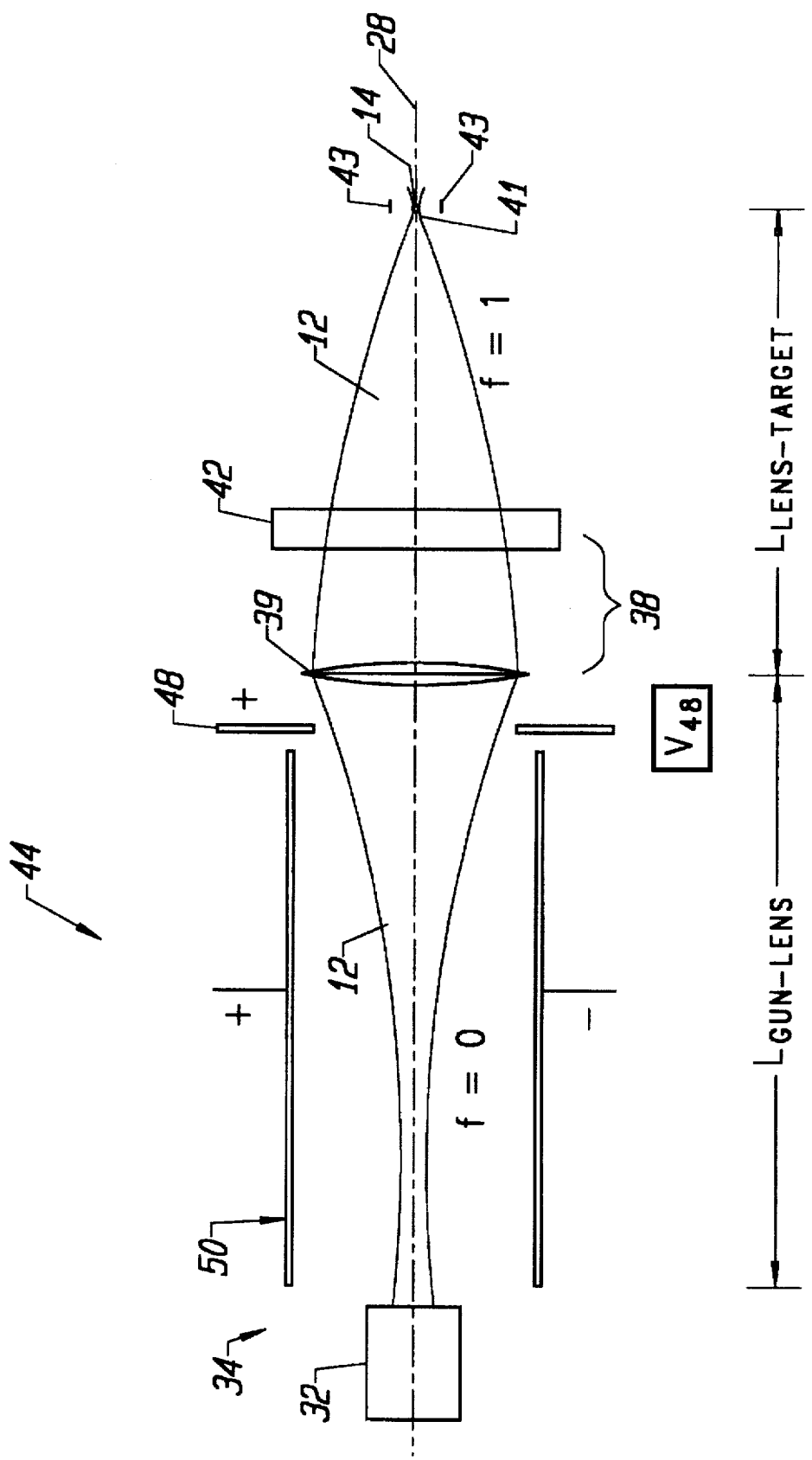
FIG. 4 depicts the upstream self-defocusing and downstream self-focusing regions of a scanning electron beam, according to the present invention.

As shown by FIG. 4, an acceptable upstream and downstream region may be produced where electrode assembly 44 includes only an ICE 50 and a PIE 48.

In the upstream region, denoted f=0, ICE 50 sweeps away positive ions and allows the electron beam 12 to self-expand. The expanded beam passes through PIE 48, and into the beam-optical system 38, more specifically through a magnetic lens 39 and deflection coils 42. Downstream (e.g., to the right) of PIE 48, denoted f=1, the electron beam 12 self-focuses (aided by the beam-optical system 38) to form a final beam spot 41 on a portion of the X-ray emitting target 14. Shown symbolically as 43, but for the present invention, the final beam spot 41 may be surrounded by a halo whose presence will degrade image definition for the entire scanning system. In the prior art, the PIE potential $V_{48}$ typically was in the +2 kV to +3 kV range, a relatively high magnitude that results in an abrupt transition region.

However, in the present invention, applicants have discovered that a substantially lower PIE potential $V_{48}$, e.g., perhaps +300 VDC rather than +2 kV to +3 kV, may be used to reduce or eliminate final beam spot haloes. As noted, spherical aberration due to non-linearity of the electron beam self-forces can occur, with the result that the beam spot at the X-ray producing target is surrounded by a halo, with resultant loss of system image definition.

Applicants have discovered that this aberration or halo appears to result from two primary causes: (i) non uniformity of current density in the electron beam produced by the electron gun, and/or (ii) non-uniform distribution of positive ions within the electron beam in the transition region between the upstream self-repulsive (space-charge dominated) and the downstream self-focusing (space-charge neutralized) regions of the beam-optical system.

Figure 5A:
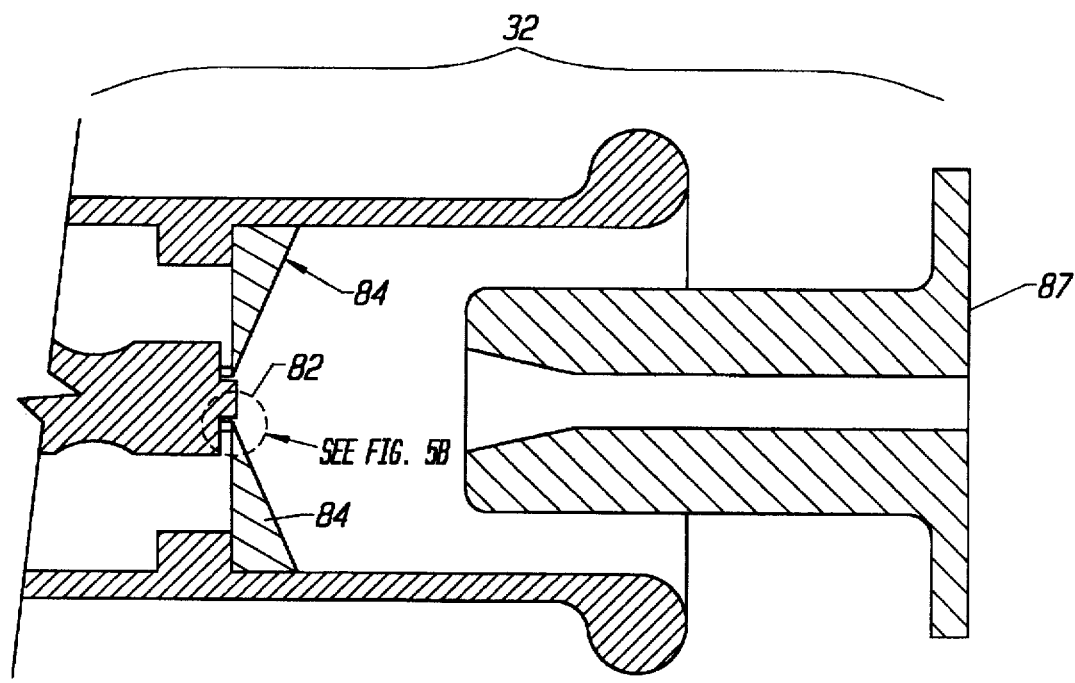
FIG. 5A depicts the electrode configuration of an electron gun found in a scanning system with which the present invention may be practiced.
Figure 5B:
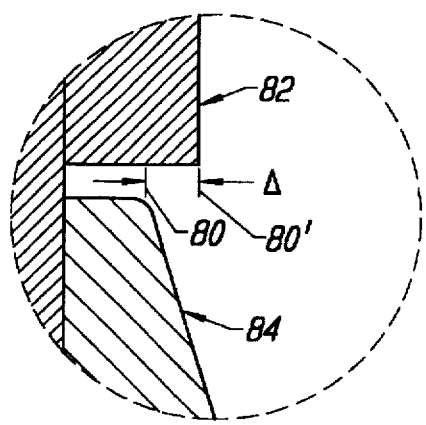
FIG. 5B is an enlarged view of the cathode projection shown in FIG. 5A, according to the present invention.

As to cause (i), non-uniformity in the electron beam is due to imperfect axial positioning of the electron gun cathode with respect to the focusing (or Pierce) electrode 84, e.g., position 80' rather than position 80 in FIGS. 5A and 5B. As to cause (ii), ion distribution in the transition region is a function of the PIE potential, which in the prior art typically has been set at a high value (up to +3 kV) to make the transition region as short as possible. FIG. 5B is an enlarged view of the circled cathode-projection 82 shown in FIG. 5A. In FIGS. 5A and 5B, the electron gun anode is denoted as 87.

The present invention minimizes beam spot halo by selecting the electron gun cathode position and the PIE potential such that their contributions to spherical aberrations cancel. In practice, cathode positioning can only be adjusted with a limited accuracy and only before assembly of the scanning system. Thus, final optimization is made by adjusting the PIE potential $V_{48}$ while observing the final beam spot profile using a W-wire or other monitor, e.g., as described in U.S. Pat. No. 4,631,741.

However, adjusting PIE potential may also vary the beam focus, as noted in U.S. Pat. No. 5,386,445. If adjustment of PIE potential is made to minimize beam halo, an independent beam focusing element must be provided, such as a magnetic solenoid lens. Of course, proper shaping of the beam spot is affected by the complete beam optics system including the focusing effects of the deflection coils and quadrupole coils.

Figure 6A:
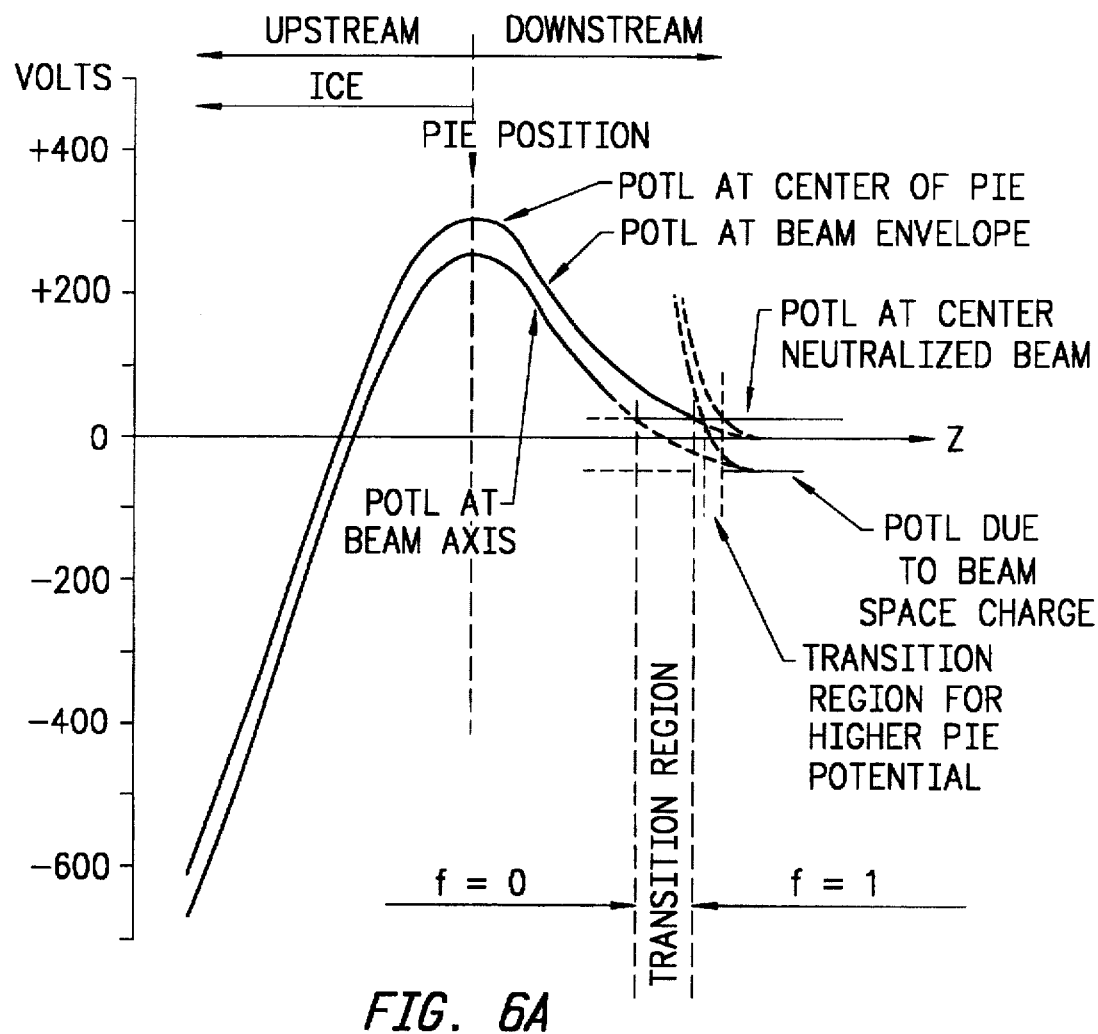
FIG. 6A depicts distribution of electron beam electrostatic potential and neutralization in the vicinity of the PIE, according to the present invention.
Figure 6B:
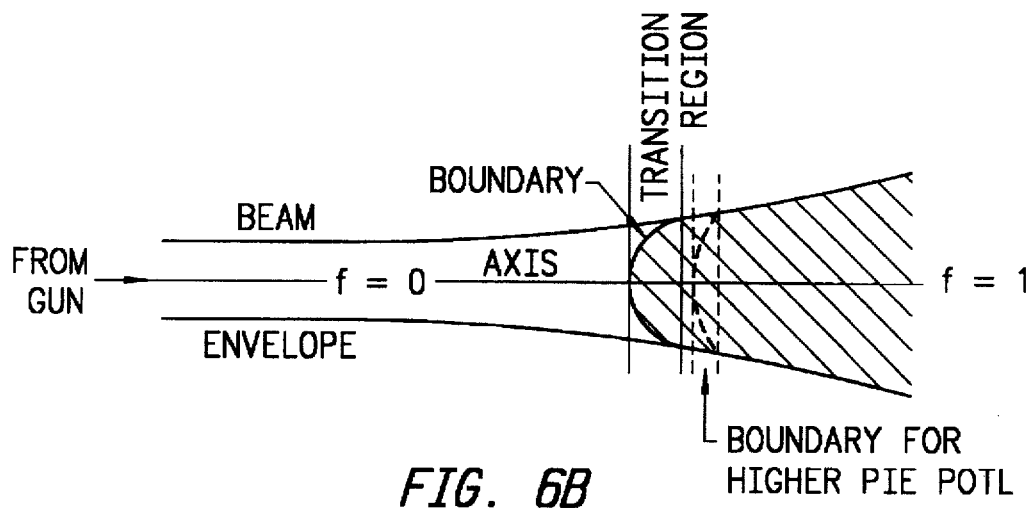
FIG. 6B depicts electron beam cross-section and neutralization distribution in the vicinity of the PIE, according to the present invention.

FIG. 6A depicts electrostatic potential distribution within the electron beam in the region of the PIE, as well as the expected neutralization distribution in the beam. As used herein, neutralization ("f") is defined as the ratio of positive ion density to beam electron density.

As shown in FIG. 6A, the potential throughout the electron beam peaks at the axial position of the PIE center. Upstream of the PIE, the potential drops rapidly to the average negative potential inside the ICE. Positive ions formed in the electron beam in this region are accelerated rapidly upstream to be removed from the beam by the ICE. Immediately downstream from the PIE the potential also drops rapidly towards the potential of the neutralized beam, a slightly positive value. Positive ions formed here are accelerated further downstream into the neutralized beam region. In the neutralized beam region, the neutralization of the beam itself is in equilibrium at a value slightly greater than unity, with the rate of electron-caused ion production being equal to the rate of loss of ions by radial flow.

Thus, there is a region of approximately zero neutralization (f=0) and a region of approximately unity neutralization (f=1). The boundary between these two regions is, to a first approximation, a paraboloid. This boundary configuration arises because the potential within the beam due to the (uniform) non-neutralized beam itself forms a parabolic trough in the radial dimension, superimposed on the potential due to the PIE. This parabolic potential trough intersects with the almost uniform potential of the neutralized beam, producing a paraboloidal boundary of the neutralized region.

This transition may be depicted as a region in which the neutralization is represented by a radial parabolic function with unit magnitude on axis, and zero magnitude at the beam envelope. As shown in FIG. 6A, the position of the transition varies with the PIE potential. More important to the present invention, however, the sharpness of the transition varies with the PIE potential, the transition increasing in sharpness with the potential. Thus, the sharpness of the transition or, equivalently, the length of the transition region may be varied by adjusting the PIE potential.

Applicants simulated operation of the present invention using the beam-sheath tracing program described by Rand, Lampel and Wang, J. Appl. Phys.62(5), p. 1639 (1987). This program operates with cylindrically symmetric beams having arbitrary initial radial current density distributions that are propagated through an idealized beam-optical system by integrating the appropriate modified Kapchinskij-Vladimirskij equations. For the simulation, a simplified beam-optical system was used, comprising a region of zero neutralization (from the electron gun, through the ICEs to the PIE), a short (but extended) transition region beyond the PIE, a thin magnetic lens, and a region of complete neutralization (from the lens to the X-ray target).

FIGS. 7A–7L depict histogram examples of the input and output of this program for certain values of the beam drift lengths, namely $L_{gun-lens}$=50 cm, $L_{lens-target}$=200 cm (see FIG. 4), using 635 mA beam current at 130 keV energy. For this configuration, the transition region was the 10 cm immediately upstream of the lens.

FIGS. 7A, 7B, 7C depict, respectively, initial beam current density distribution, radial neutralization distribution in the transition region, and an Abel transform of the final beam spot target-location current density distribution. In these figures, as well as FIGS. 7D–7L, the horizontal axis represents radius with full scale value 0.28 cm for FIGS. 7A, 7B, 7D, 7E, 7G, 7H, 7J, 7K, and 0.14 cm full scale value for FIGS. 7C, 7F, 7I, and 7L. In these figures, the vertical axis is in relative units.

In practice, the final beam spot pulse form can be observed with a monitoring wire such as disclosed in U.S. Pat. No. 4,631,741.

In FIGS. 7A, 7B, 7C an ideal initial uniform beam with zero neutralization in the transition region is assumed.

FIGS. 7D, 7E, 7F depict respectively, initial beam current density distribution, radial neutralization distribution in the transition region, and an Abel transform of the final beam spot target-location current density distribution for an initial beam with a "domed" parabolic radial beam current density distribution, with zero neutralization in the transition region.

FIGS. 7G, 7H, 7I depict respectively, initial beam current density distribution, radial neutralization distribution in the transition region, and an Abel transform of the final beam spot target-location current density distribution for an ideal initial uniform beam with a parabolic distribution of neutralization in the transition region.

FIGS. 7J, 7K, 7L depict respectively, initial beam current density distribution, radial neutralization distribution in the transition region, and an Abel transform of the final beam spot target-location current density distribution for a parabolic radial beam distribution with the parabolic neutralization distribution, in which the two distributions were chosen to minimize the halo in the final beam spot.

FIGS. 7A, 7B, 7C demonstrate that a uniform beam remains uniform if the transition between the two beam regions is infinitely sharp. This results in the best possible final beam spot. By contrast, FIGS. 7D, 7E, 7F depict how a domed initial beam distribution forms a halo around a sharp beam spot, a situation typical of spherical aberration. FIGS. 7G, 7H, 7I demonstrate that even with an ideal beam, the neutralization distribution in the transition region can nonetheless produce a beam halo.

Significant to the present invention, FIGS. 7J, 7K, 7L demonstrate that the neutralization distribution in the transition region may be used to minimize the halo resulting from an initial non-uniform domed beam distribution. In these figures, final beam spot intensity is 97% of that which can be achieved from an ideal system, using a current density distribution that drops by 25% from the Z-axis to the beam edge, and a neutralization amplitude of 0.36 in a transition region that is 10 cm in length, which corresponds to 3.6 cm actual transition length.

It is noted that an initially "dished" electron gun beam distribution in which current density is higher at the edge than at the center cannot be corrected with this beam geometry. Further, since some non-uniformity of neutralization in the transition region must occur, even with high PIE potential, the range of correctable domed beam distributions may be limited. However, as the initial drift length increases, the situation reverses and only dished distributions are correctable according to the present invention.

In the simulations of FIGS. 7A–7L, electron gun-produced beam characteristics were calculated using the Stanford Linear Accelerator Center EGUN program (document SLAC-226). Electron gun geometries similar to that described in U.S. Pat. No. 4,621,213 were used, with the electron gun cathode 82 protruding by various amounts $\Delta$ with respect to the focusing (Pierce) electrode 84 (see FIG. 5A).

Figures 8A, 8C:
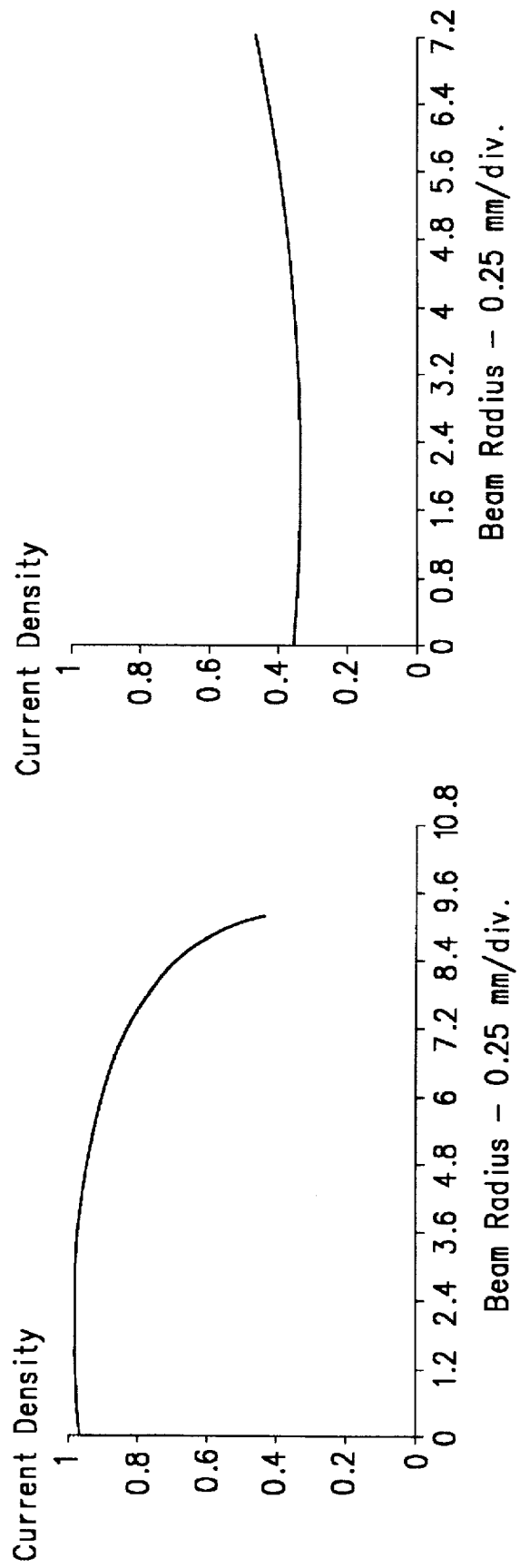
FIGS. 8A–8B and FIGS. 8C–8D depict, for respective high and low electron gun cathode positions, current density, and phase space distributions inside the electron gun anode, according to the present invention.
Figures 8B, 8D:
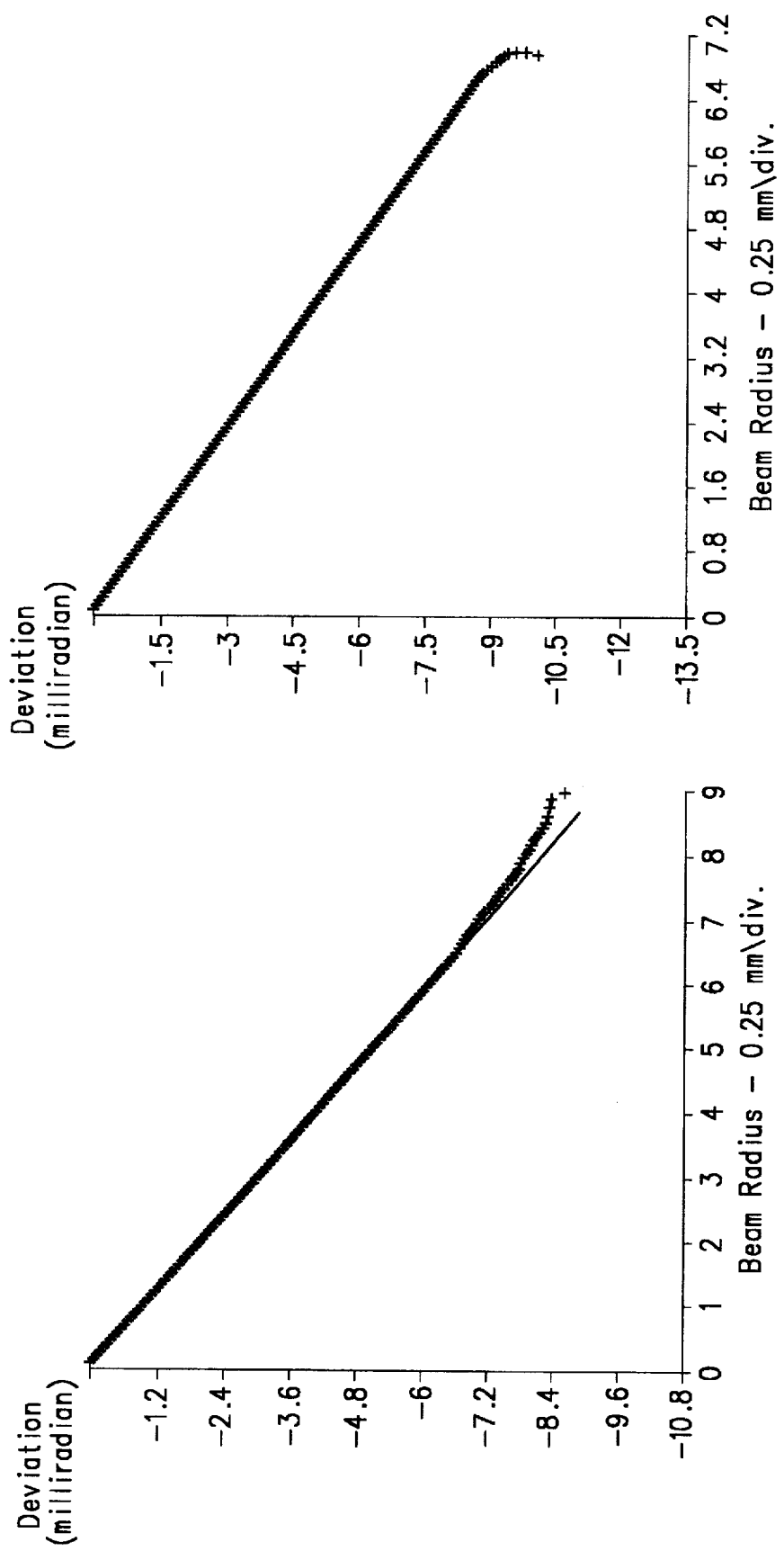

For respective high (i.e., more protruding) and low cathode positions, FIGS. 8A–8B, and FIGS. 8C–8D depict radial distributions of beam current density, and phase space at a point within the electron gun anode for beam radii 2.25 mm (FIGS. 8A, 8B) and 1.75 mm (FIGS. 8C, 8D). In FIGS. 8A and 8C, current density is shown in arbitrary units along the vertical axis, and in FIGS. 8B and 8D the vertical axes are deviations in milliradians.

With respect to FIGS. 5A and 5B, the high cathode position (FIGS. 8A, 8B) and low cathode positions (FIGS. 8C, 8B) represent a change in cathode position, $\Delta$ of 0.1 mm. These high and low cathode configurations span the condition of an "ideal" uniform beam. FIGS. 8A–8B demonstrate that production of a domed beam distribution (whose aberration can be corrected in the specified geometry) requires cathode placement in the focusing electrode higher than that for a uniform beam. Further, the beam-sheath analysis demonstrates that beam spot halo due to the calculated domed beam distribution is substantially (e.g., almost completely) eliminated.

Applicants experimentally confirmed the above simulation-predictions using an electron beam tomographic scanning system as depicted in FIG. 2. The electron gun was operated at a beam current of 635 mA and a −135 kV cathode potential. The $L_{gun-lens}$ distance was approximately 50 cm, and the $L_{lens-target}$ distance approximately 200 cm. The cathode was adjusted for each of the conditions specified herein for the EGUN calculations, and as depicted in FIGS. 8A–8D.

Figure 9:
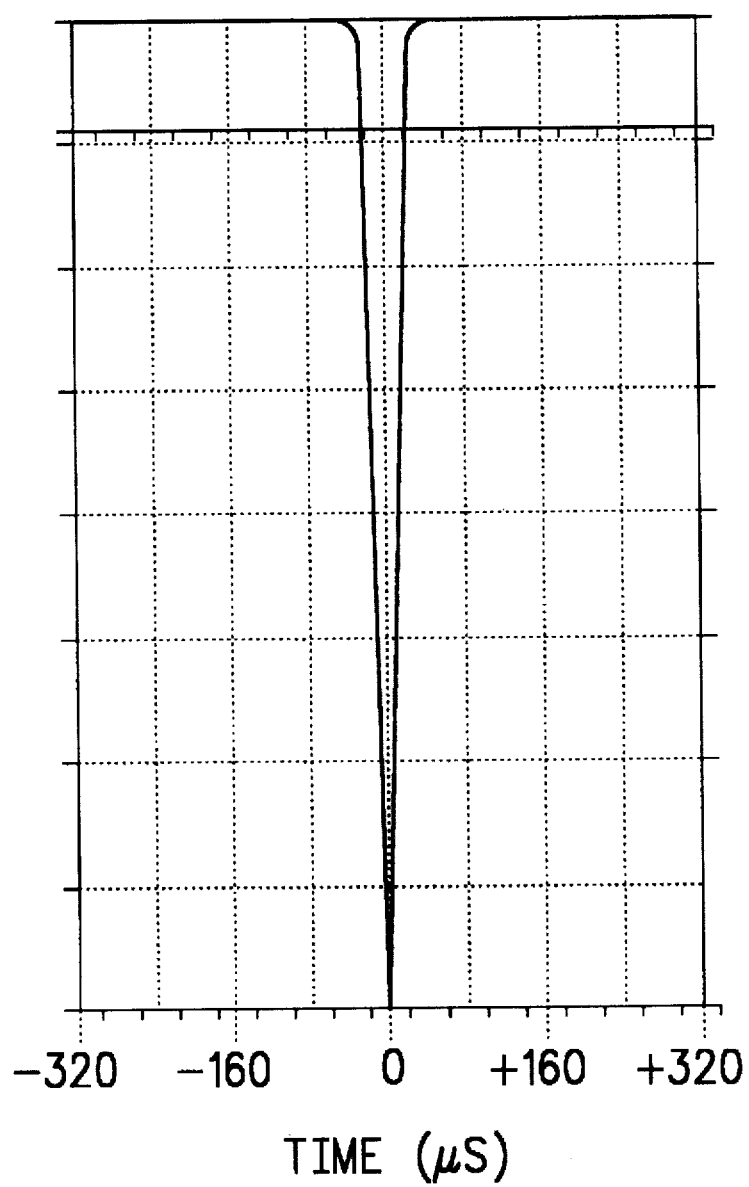
FIG. 9 depicts a signal from a typical W-wire representing a substantially halo-free beam spot profile, produced according to the present invention.

It was found that with the cathode recessed too far in the focusing electrode (dished distribution case), the beam halo could not be eliminated by adjusting the PIE potential. However, with the cathode high, domed distribution case, the beam halo could be reduced to a negligible magnitude by setting the PIE potential in the +100 VDC to +1500 VDC range. An example of the resulting substantially halo-free beam spot profile is shown in FIG. 9, in which 80 µs corresponds to 2.6 mm, and a 100 ms scan time was used.

As used herein, the expression "at least reduced" means that the beam halo is reduced in size, if not actually eliminated, by the present invention.

Modifications and variations may be made to the disclosed embodiments without departing from the subject and spirit of the invention as defined by the following claims. For example, although a spherical aberration reducing method has been described for use in a scanning electron beam CT system, the method could be applied to other applications as well, e.g., high current electron accelerator injectors, and possibly electron beam welders.

What is claimed is:

1. A method for reducing spherical aberration at the beam spot in an electron beam generated in a scanning electron beam CT X-ray system that includes an electron gun cathode mounted within a vacuum housing chamber having an up-stream region wherein the electron beam expands and having a downstream region wherein the electron beam converges to form the beam spot, and a beam-optical system including a magnetic lens for focussing and scanning said beam spot along an X-ray emitting target, the method including the following steps:

(a) disposing said electron gun cathode substantially on an axis projecting through said vacuum housing chamber at a location whereat non-uniformity of current density in said electron beam contributes a first effect to spherical aberration;

(b) disposing a positive ion electrode (PIE) downstream from and substantially coaxially with said electron gun, said PIE being coupled to a positive potential whose magnitude affects positive ion distribution in a transition region of said electron beam and contributes a second effect to spherical aberration;

(c) selecting said magnitude of said positive potential such that said second effect substantially cancels said first effect;

wherein said halo around said beam spot at said X-ray emitting target is at least reduced.

2. The method of claim 1, wherein step (c) includes monitoring a profile of said beam spot while selecting said magnitude of said positive potential.

3. The method of claim 1, wherein said PIE is a planar disk having a central opening sized to permit passage of said electron beam therethrough.

4. The method of claim 1, wherein said positive potential has a magnitude ranging from about +100 VDC to about +1500 VDC.

5. The method of claim 1, wherein said CT system includes an ion clearing electrode (ICE) unit, mounted upstream from and substantially coaxially with said PIE, coupled to an ICE potential source causing said ICE to produce a field sweeping away positive ions in said upstream region.

6. The method of claim 1, wherein said CT system includes a periodic ion clearing electrode (PICE) unit, mounted upstream from and substantially coaxially with said PIE, coupled to sources of PICE potential causing said PICE to create alternating axial electric fields that remove positive ions in said upstream region.

7. The method of claim 1, wherein said CT system includes a rotatable ion clearing electrode (RICE) unit, mounted upstream from and substantially coaxially with said PIE, coupled to sources of RICE potential causing said RICE to create transverse electric fields that remove positive ions in said upstream region.

8. The method of claim 1, wherein following steps (a), (b), and (c), said electron beam is focused using said magnetic lens.

9. The method of claim 1, wherein at step (b), said positive ion distribution is varied in a direction normal to said axis of said scanner.

* * * * *